(12) United States Patent
Wieselblad et al.

(10) Patent No.: US 8,617,124 B2
(45) Date of Patent: Dec. 31, 2013

(54) MEDICAMENT DELIVERY DEVICE

(75) Inventors: Anders Wieselblad, Stockholm (SE);
Kenny Kai Fung Cheung, Bromma (SE)

(73) Assignee: SHL Group AB, Nacka Strand (SE)

( * ) Notice: Subject to any disclaimer, the term of this patent is extended or adjusted under 35 U.S.C. 154(b) by 30 days.

(21) Appl. No.: 13/376,283

(22) PCT Filed: Jul. 5, 2010

(86) PCT No.: PCT/SE2010/050769
§ 371 (c)(1),
(2), (4) Date: Feb. 16, 2012

(87) PCT Pub. No.: WO2010/140974
PCT Pub. Date: Dec. 9, 2010

(65) Prior Publication Data
US 2012/0136315 A1    May 31, 2012

Related U.S. Application Data

(60) Provisional application No. 61/184,626, filed on Jun. 5, 2009.

(30) Foreign Application Priority Data

Aug. 21, 2009  (SE) ...................................... 0950595

(51) Int. Cl.
*A61M 5/00*  (2006.01)
(52) U.S. Cl.
USPC .......... 604/208; 604/71; 604/97.03; 604/189; 604/211
(58) Field of Classification Search
CPC ..................................................... A61M 5/00
USPC ......... 604/71, 97.03, 189, 207, 208, 211, 246
See application file for complete search history.

(56) References Cited

U.S. PATENT DOCUMENTS 4,936,833 A * 6/1990 Sams ............................ 604/232
5,921,966 A * 7/1999 Bendek et al. ................ 604/207
(Continued)

FOREIGN PATENT DOCUMENTS

WO    2010/140974 A1    12/2010

OTHER PUBLICATIONS

Swedish Patent Office, Intl Search Report in PCT/2010/050769, Sep. 16, 2010.

(Continued)

*Primary Examiner* — Nicholas Lucchesi
*Assistant Examiner* — Gerald Landry, II
(74) *Attorney, Agent, or Firm* — Potomac Patent Group PLLC

(57) ABSTRACT

The present invention relates to a medicament delivery device comprising an elongated housing arranged to contain a medicament container which medicament container contains a number of doses; a dose counter mechanism comprising a dose drum arranged with dose indicia on its outer surface and visible through a window on said housing; a rotatable driver connected to said dose drum; a plunger rod arranged to act on said medicament container for expelling a dose of medicament; an actuation mechanism connected to said rotatable driver and to said plunger rod when said medicament delivery device is actuated; wherein said dose drum is arranged with internal threads, in engagement with corresponding threads on said driver, wherein said threads have a certain pitch; wherein said dose drum is also arranged with external threads in engagement with corresponding threads arranged fixed in relation to said housing, wherein said threads have a certain pitch; and wherein the pitch of the threads between the dose drum and fixed in relation to the housing is lesser than the threads between the dose drum and the driver such that when said driver is rotated a certain angular distance, said dose drum is rotated a lesser angular distance.

9 Claims, 15 Drawing Sheets

(56) References Cited

U.S. PATENT DOCUMENTS

| | | | |
|---|---|---|---|
| 6,228,067 B1* | 5/2001 | Gabriel | 604/211 |
| 7,896,850 B2* | 3/2011 | Kronestedt et al. | 604/211 |
| 8,187,233 B2* | 5/2012 | Harms et al. | 604/207 |
| 8,267,900 B2* | 9/2012 | Harms et al. | 604/207 |
| 2004/0019333 A1* | 1/2004 | Graf et al. | 604/207 |
| 2005/0137571 A1 | 6/2005 | Hommann | |
| 2007/0233015 A1* | 10/2007 | Saiki | 604/207 |
| 2007/0299406 A1 | 12/2007 | Burren et al. | |
| 2008/0077095 A1 | 3/2008 | Kirchhofer | |
| 2008/0281275 A1* | 11/2008 | Moller | 604/224 |
| 2008/0287883 A1* | 11/2008 | Radmer et al. | 604/211 |
| 2008/0312605 A1* | 12/2008 | Saiki | 604/211 |
| 2009/0299797 A1* | 12/2009 | Kaczmarek et al. | 705/8 |
| 2010/0179485 A1* | 7/2010 | Radmer et al. | 604/189 |
| 2010/0331791 A1* | 12/2010 | Plumptre | 604/207 |

OTHER PUBLICATIONS

Swedish Patent Office, Written Opinion in PCT/2010/050769, Sep. 16, 2010.
Request to Restore Priority in PCT/2010/050769, Jul. 10, 2010.
Swedish Patent Office, Notice of Intended Refusal of Request to Restore Priority in PCT/2010/050769, Jul. 19, 2010.
Swedish Patent Office, Decision on Request to Restore Priority in PCT/2010/050769, Sep. 27, 2010.

* cited by examiner

MEDICAMENT DELIVERY DEVICE

TECHNICAL AREA

The present invention relates to a medicament delivery device arranged with a dose information mechanism.

TECHNICAL BACKGROUND

There are a number of medicament delivery devices on the market that are intended for self-administration. These devices have different degrees of functionality and thus complexity both regarding number of interacting components and handling of the actual device for delivering a dose of medicament.

In order that the patient or user is alerted regarding the state of the device for example regarding the number of doses that have been delivered or are remaining as well as the dose size, if the user may set different dose sizes, some devices are arranged with indicia visible through openings or windows in the device for mechanical dose information mechanisms or electronic displays if the device is provided with electronic dose information mechanisms.

Regarding mechanical dose information mechanisms, indicia are often arranged on an outer surface of a rotatingly arranged member, which during dose setting and/or dose delivery rotates a certain amount, which is displayed in the opening or window of the device. This function is adequate for many devices where the doses are rather large and/or that the rotation of the dose information member is to such an extent that all the indicia to be shown can fit onto the surface of the member.

However, for some devices and in particular when the dose increments are rather small, or the movement of the indicia member is rather small for a set dose, all indicia to be shown cannot fit onto the surface of the member which leads to problem regarding providing the user with the appropriate information.

There is thus a need for improvement regarding mechanical dose information mechanisms that also can handle small dose increments such that the proper information is provided to the user, e.g. having some sort of transmission or the like in order to handle movement of components of a medicament delivery device.

U.S. Pat. No. 6,004,297 discloses an injection syringe comprising a housing, a piston rod with a non-circular cross-section and an outer thread, a piston rod drive which includes a piston rod guide mating with the cross-section of the piston rod, and a nut which is not axially displaceable and which mates with the thread of the piston rod to form a self-locking thread connection.

Rotation of a dose setting element causes an injection button to be screwed out to project from the housing. When the injection button is pushed axially, such axial movement is transformed, by way of the threaded coupling, into a rotation of one of the piston drive elements relative to the other one. A unidirectional coupling between the nut member and the piston rod guide allows rotation in one direction by which the piston rod is transported in a distal direction. The coupling has an initial reluctance to be overcome before rotation takes place, said reluctance being large enough to resist torques exerted during the dose setting.

U.S. 2008/287,883 discloses an injection device for apportioning set doses of a drug from a reservoir to a subject. The injection device comprises a housing having an interior thread formed as an outwardly pointing thread carried on an upstanding tower centrally located in the pen shaped device. This outwardly pointing thread forms a first thread connection with the interior thread of the rotatable scale drum. The injection device further comprises a driver for moving the piston rod forward when moved axially. The driver operates the piston rod through a second thread connection having a pitch different than the first thread connection.

Non of the documents do however address the problem with displaying dose information in connection with mechanical devices for all types of dose sizes and dose increments.

BRIEF DESCRIPTION OF THE INVENTION

The aim of the present invention is to remedy the drawbacks of the state of the art devices and to provide a dose information mechanism capable of mechanically handling and displaying dose information in a wide range of dose quantities.

This aim is obtained by the features of the independent patent claims. Preferable embodiments of the invention form the subject of the dependent patent claims.

According to a main aspect of the invention it is characterised by a medicament delivery device comprising an elongated housing arranged to contain a medicament container which medicament container contains a number of doses; a dose counter mechanism comprising a dose drum arranged with dose indicia on its outer surface and visible through a window on said housing; a rotatable driver connected to said dose drum; a plunger rod arranged to act on said medicament container for expelling a dose of medicament; an actuation mechanism connected to said rotatable driver and to said plunger rod when said medicament delivery device is actuated; wherein said dose drum is arranged with internal threads, in engagement with corresponding threads on said driver, wherein said threads have a certain pitch; wherein said dose drum is also arranged with external threads in engagement with corresponding threads arranged fixed in relation to said housing, wherein said threads have a certain pitch; and wherein the pitch of the threads between the dose drum and fixed in relation to the housing is lesser than the threads between the dose drum and the driver such that when said driver is rotated a certain angular distance, said dose drum is rotated a lesser angular distance.

There are a few advantages with the present invention. The use of a driver having a thread with a first pitch and a dose drum having a thread with a second pitch that is lesser than the first pitch a gearing down of the rotation of the dose drum is obtained. This facilitates greatly the possibilities of displaying a large number of doses and/or small doses that otherwise would not be feasible, at least not if the device is to be kept within a reasonable size. The advantage is also that the mechanism for displaying doses can be kept all-mechanical. There is thus no need for costly battery-driven electronic display solutions which tend to break more easily if the device is dropped and which tend to not function if the batteries are depleted. Then there is no information whatsoever if the device is handled until new batteries are inserted.

As seen the dose information mechanism according to the present invention may be utilized with both manually operated devices as well as devices having automatic functions. In this respect it is to be understood that also other functions may be automated such as the mixing and the penetration function.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
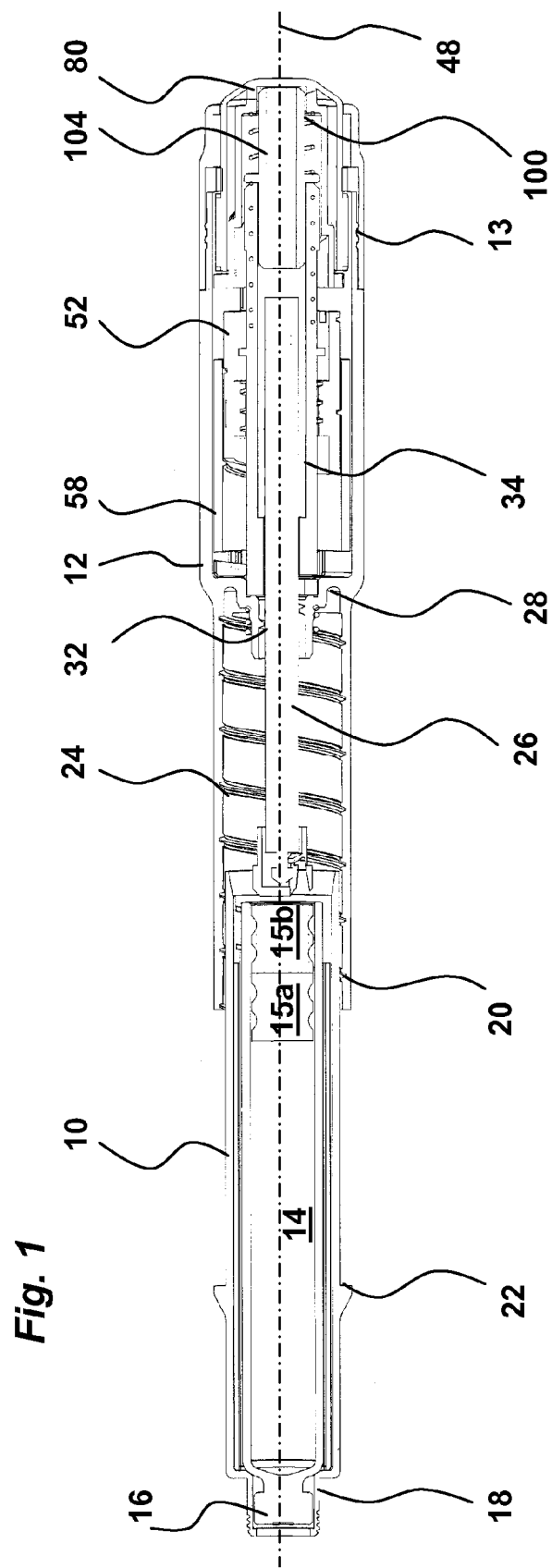
FIG. 1 shows a side view in cross-section of a first embodiment of a medicament delivery device according to the present invention.

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient.

The medicament delivery device shown in the drawings and comprising the present invention comprises:

an elongated housing arranged to contain a medicament container 14; 116, which medicament container contains a number of doses;

a dose counter mechanism comprising a dose drum 52; 162 arranged with dose indicia 56; 172 on its outer surface and visible through a window on said housing;

a rotatable driver 34; 152 connected to said dose drum;

a plunger rod 26; 134 arranged to act on said medicament container for expelling a dose of medicament;

an actuation mechanism connected to said rotatable driver and to said plunger rod when said medicament delivery device is actuated; wherein said dose drum 52; 162 is arranged with internal threads 50; 164, in engagement with corresponding threads 42; 154 on said driver, wherein said threads have a certain pitch; wherein said dose drum 52; 162 is also arranged with external threads 54; 166 in engagement with corresponding threads 60; 168 arranged fixed in relation to said housing, wherein said threads have a certain pitch; and wherein the pitch of the threads 54, 166; 60, 168 between the dose drum and fixed in relation to the housing is lesser than the threads 50, 164; 42, 154 between the dose drum and the driver such that when said driver is rotated a certain angular distance, said dose drum is rotated a lesser angular distance.

In a first embodiment of the invention shown in the drawings 1-10, the elongated housing comprises a proximal housing part 10, a distal housing part 12 as well as a distal end cap 13. It is however to be understood that the housing of the device may have other configurations within the scope of the invention. Inside the proximal housing part the medicament container 14 can be placed, in the shown first embodiment a so called dual chamber medicament container arranged with two stoppers 15*a*, 15*b*. The proximal end of the medicament container is arranged with a neck 16, which neck 16 fits into a neck 18 at the proximal end of the proximal housing part. The latter neck 18 is arranged with attachment means for detachably attaching a medicament delivery member such as an injection needle, a nozzle, mouthpiece or the like (not shown). The attachment means could be any suitable means such as threads, bayonet fittings, snap-on mechanisms and the like.

The outer distal surface of the proximal housing part 10 is arranged with threads 20 as well as a circumferentially extending ledge 22. The threads 20 are designed to cooperate with threads 24 arranged on an inner surface of the distal housing part 12. Inside the distal housing part 12 the plunger rod 26 is arranged and extending through a wall part 28. The plunger rod is arranged with threads 30 where a passage 32 through the wall part 28 is provided with corresponding threads, FIG. 2. Outside the plunger rod 26, the driver 34 is arranged. The proximal end of the driver 34 is arranged with radially inwardly directed protrusions 36, FIG. 5. The plunger rod 26 is further arranged with longitudinally extending grooves 38, FIG. 5, in which the protrusions 36 fit, as to provide a lock against rotation of the plunger rod 26 in relation to the driver 34, as will be described below. The proximal end of the driver 34 is arranged with flexible arms 40, FIG. 5, cooperating with a circumferential surface of the wall 28 such that the driver 34 can only rotate in one direction. The outer surface of the driver 34 is arranged with threads 42 as well as a circumferentially running ledge 44, FIG. 2. Further, the distal circumference part of the driver is arranged with a number of positioned ledges 46, wherein the ledges 46 have a predetermined number of degrees to each other corresponding to the predetermined amount of medicament to be delivered. Further, the ledges 46 have inclined surfaces in relation to the longitudinal direction 48 of the device, FIG. 2, the function of which will be described below.

Figure 4:
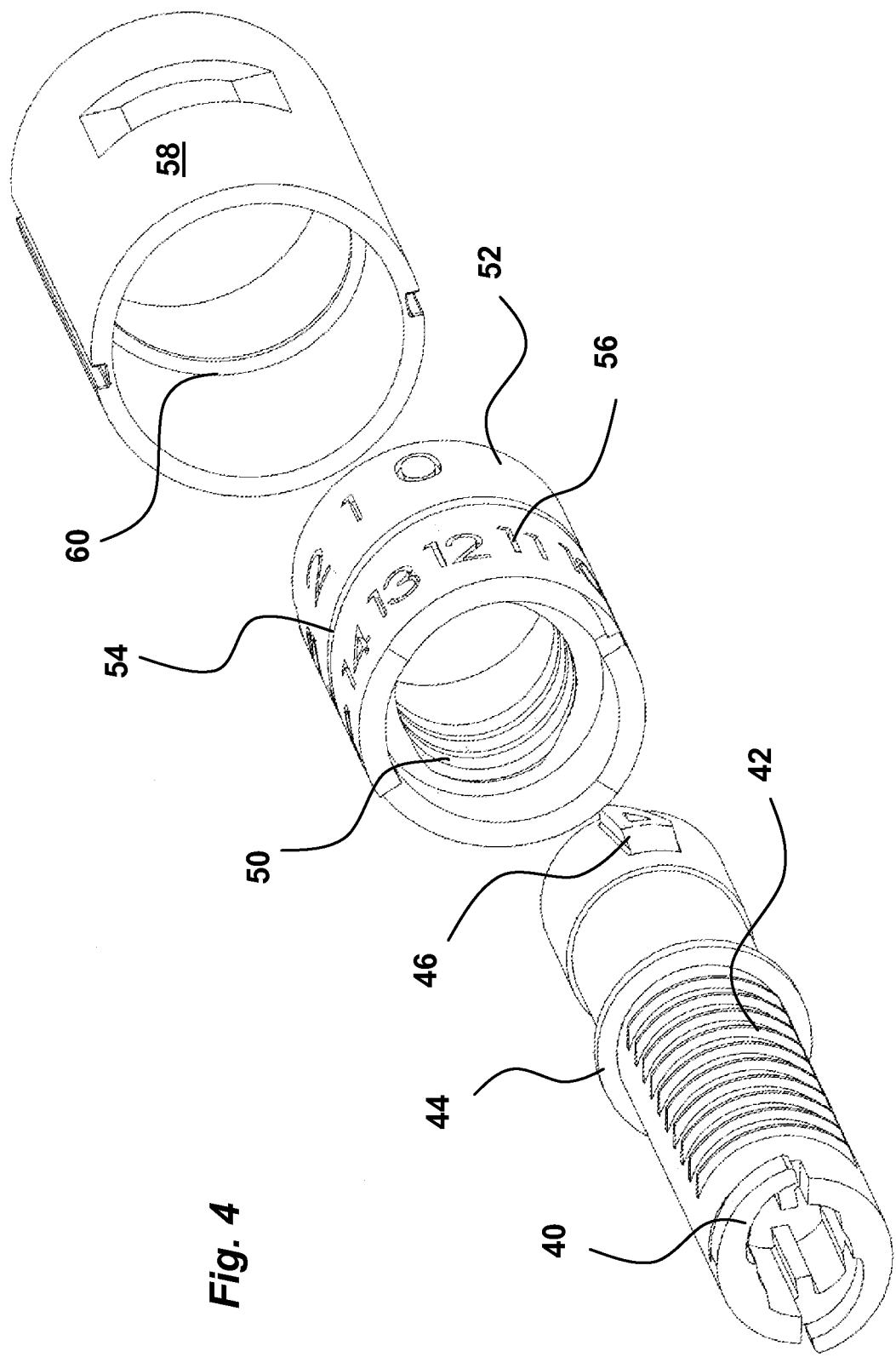
FIG. 4 shows a detailed exploded view of a dose counter mechanism according to the present invention.

The threads 42 of the driver 34 are arranged to cooperate with internal threads 50 of a tubular shaped member, which is the dose drum 52, FIG. 4. The outer surface of the dose drum 52 is arranged with a spirally extending thread 54 as well as indicia 56, such as numbers, indicating a dose number which is visible through an opening or window on the distal housing part as will be explained below.

Figure 8:
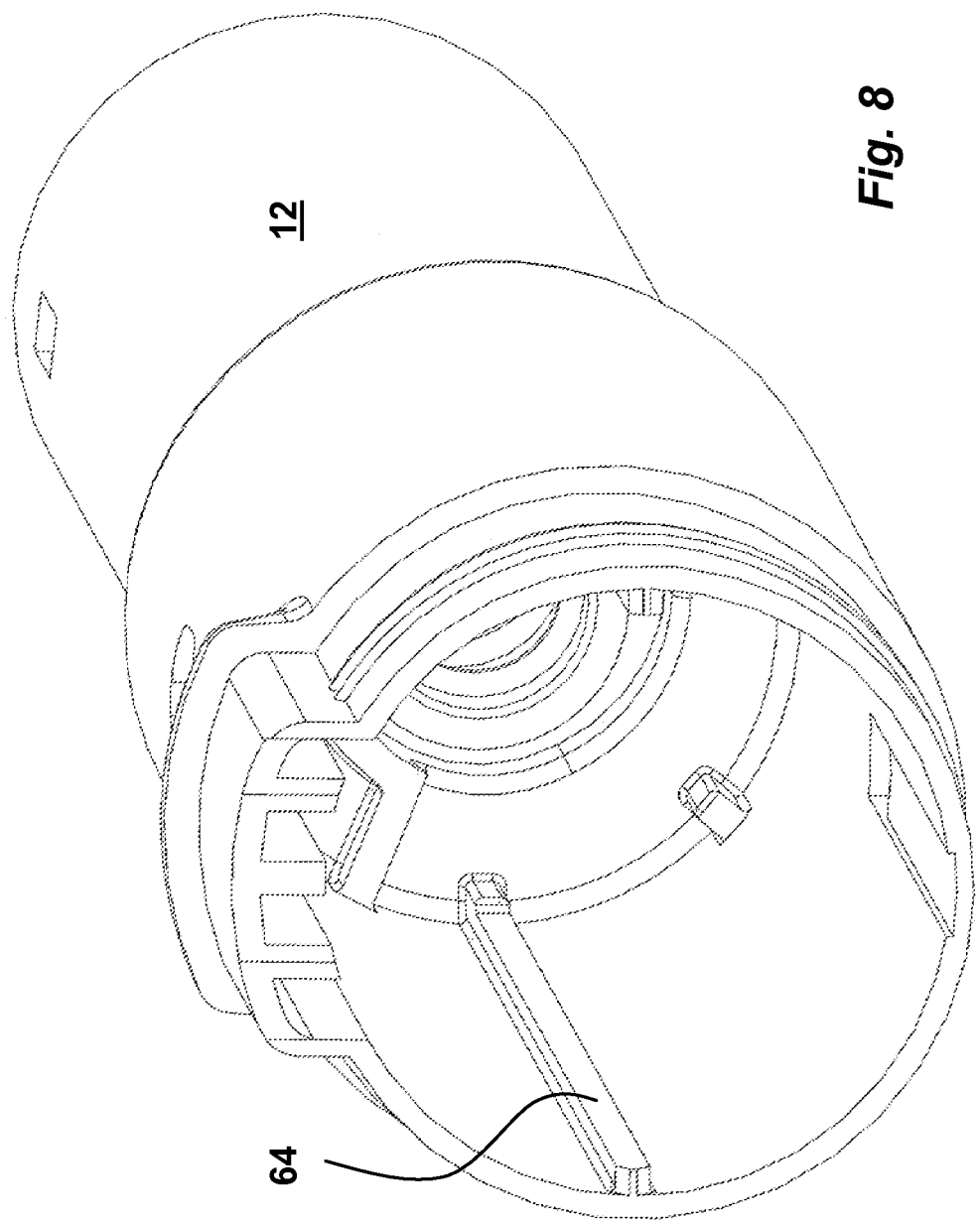
FIG. 8 shows a detailed view of a distal housing part.

The dose counter mechanism further comprises a generally tubular shaped member 58, hereafter named thread drum, coaxially arranged on the dose drum. The thread drum 58 is arranged with a spirally running thread 60 on its inner surface, which thread 60 is arranged to cooperate with the spiral thread 54 of the dose drum 52, FIG. 4. It is also conceivable that the thread 54 of the dose drum is arranged to cooperate with threads on the inner surface of the distal housing part. The thread drum 58 is locked against rotation by longitudinally extending grooves 62 on the outer surface of the thread drum, FIG. 4, cooperating with longitudinally extending ribs 64 arranged on the inner surface of the distal housing part 12, FIG. 8. Therefore, the thread 54 of the dose drum 52 cooperates with the thread 60 arranged on the inner surface of the thread drum which is fixed in relation to the distal housing part 112.

The actuation mechanism of the first embodiment comprises a toggle sleeve 66 and an actuation button 80, wherein the actuation button is operably connected to the toggle sleeve and the toggle sleeve is operably connected to the driver 34 such that the driver is rotated when said actuation button 80 is actuated, the function of which will be described below.

Figure 5:
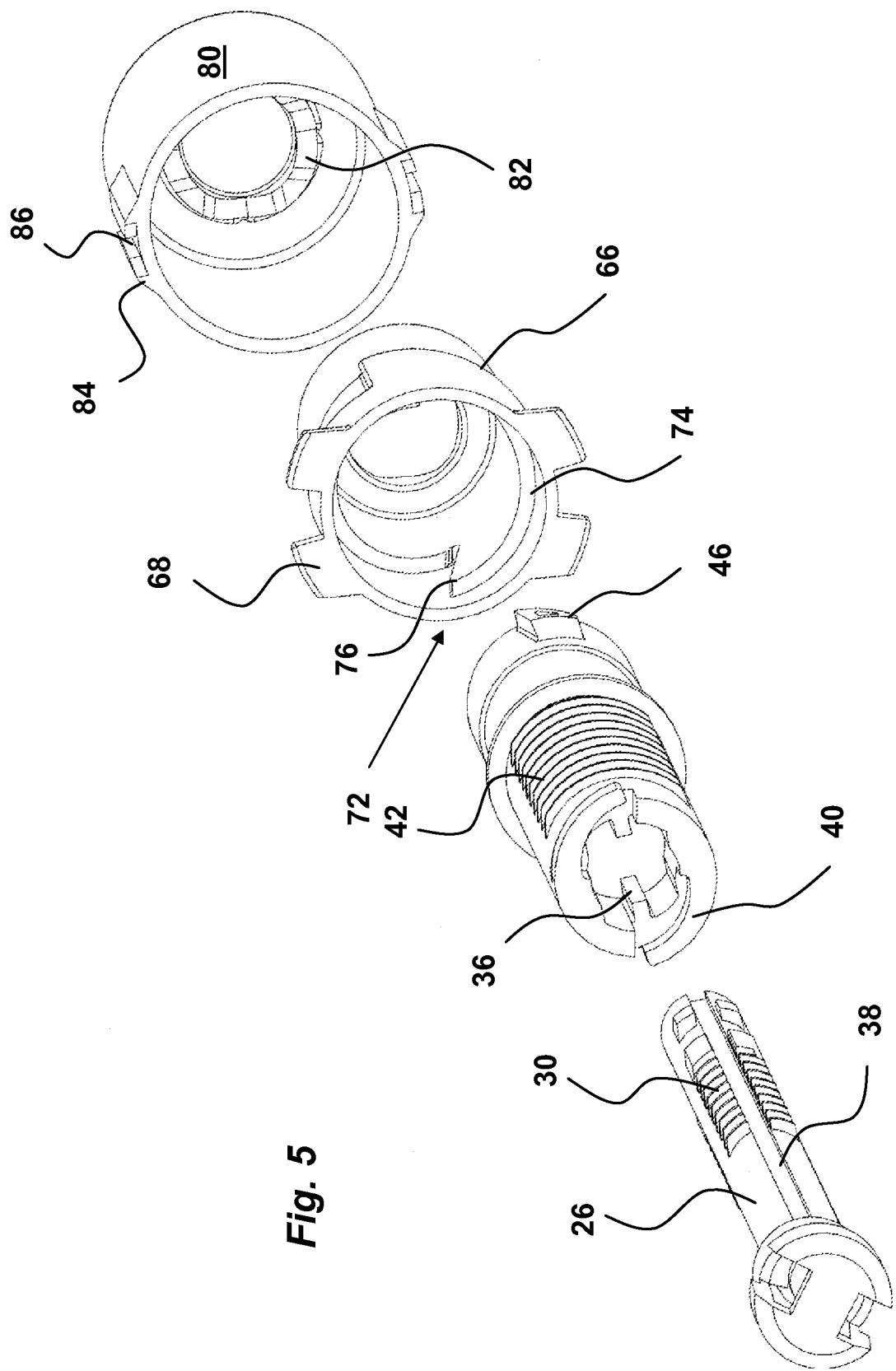
FIG. 5 shows a detailed exploded view of an actuation mechanism according to the present invention.

The distal part of the driver 34 is in contact with a sleeve-shaped member, which is the toggle sleeve 66, FIG. 5. The proximal end of the toggle sleeve 66 is arranged with two sets of generally radially outwardly extending lips 68, intended to interact with the longitudinally extending ribs 64 on the inner surface of the distal housing part such as to only admit a certain rotational movement of the toggle sleeve 66 as will be described below.

Figure 6:
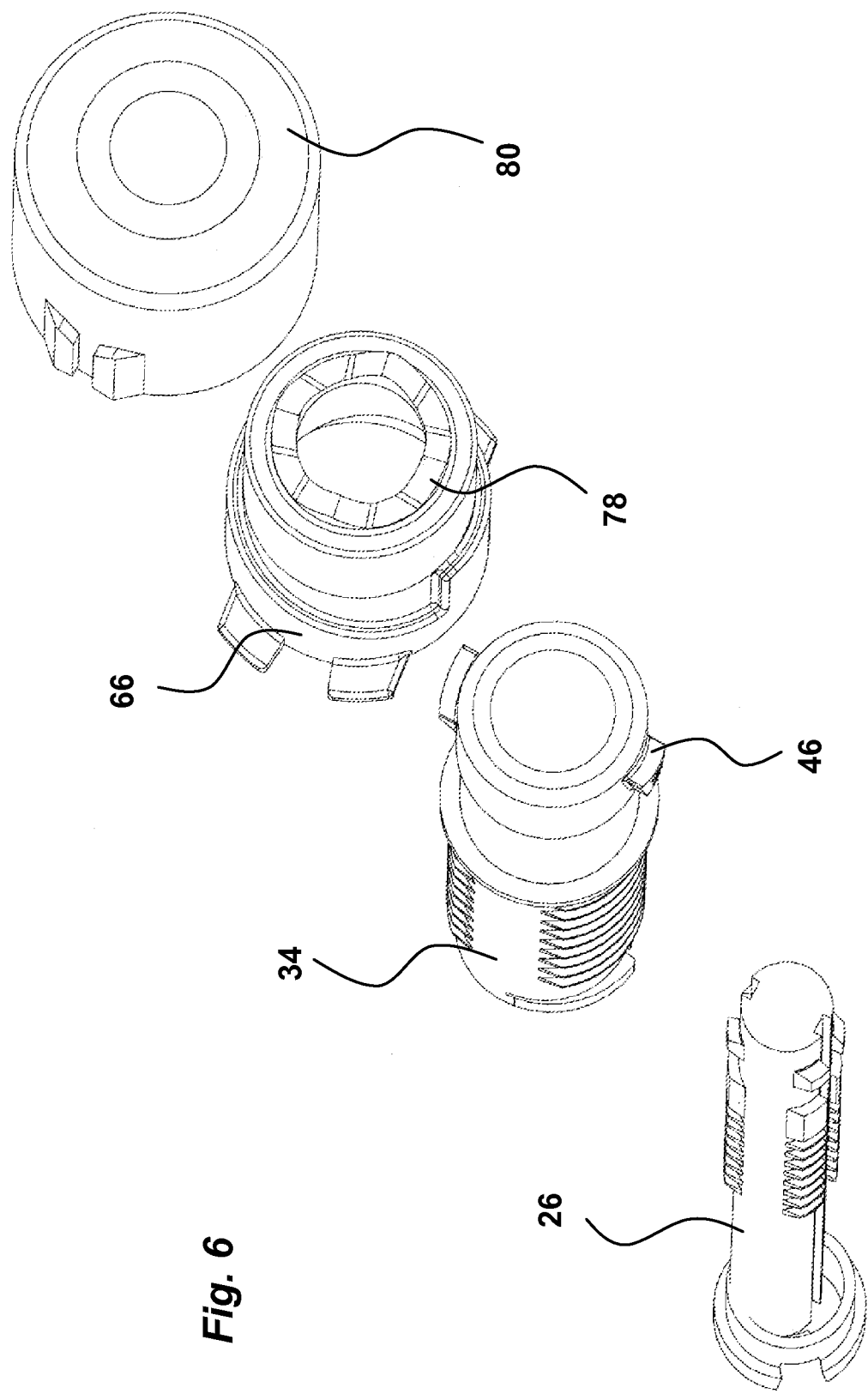
FIG. 6 shows the mechanism of FIG. 5 rotated 180°.

As shown in FIG. 5, the inner surface of the toggle sleeve 66 is arranged with ledges 72 directed in the proximal direction, which ledges are shaped with inclined sections 74, separated by stepwise transitions 76. These ledges 72 are arranged to cooperate with the inclined ledges 46 of the driver 34 as will be described. The distal end surface of the toggle sleeve 66 is further arranged with a zig-zag-shaped circular surface 78, FIG. 6.

As shown in FIG. 5, the actuation button 80 is arranged outside the toggle sleeve 66, having a generally tubular shape. The inner end surface of the actuation button is arranged with a zig-zag-shaped circular surface 82 which is intended to co-act with the zig-zag-shaped circular surface 78 of the toggle sleeve 66. On the outer side surface of the actuation button 80 two outwardly directed protrusions 84 are arranged on opposite sides, which protrusions 84 are arranged with longitudinally directed grooves 86 that in turn are arranged to cooperate with the same longitudinally extending protrusions 64 as the dose drum.

Figure 2:
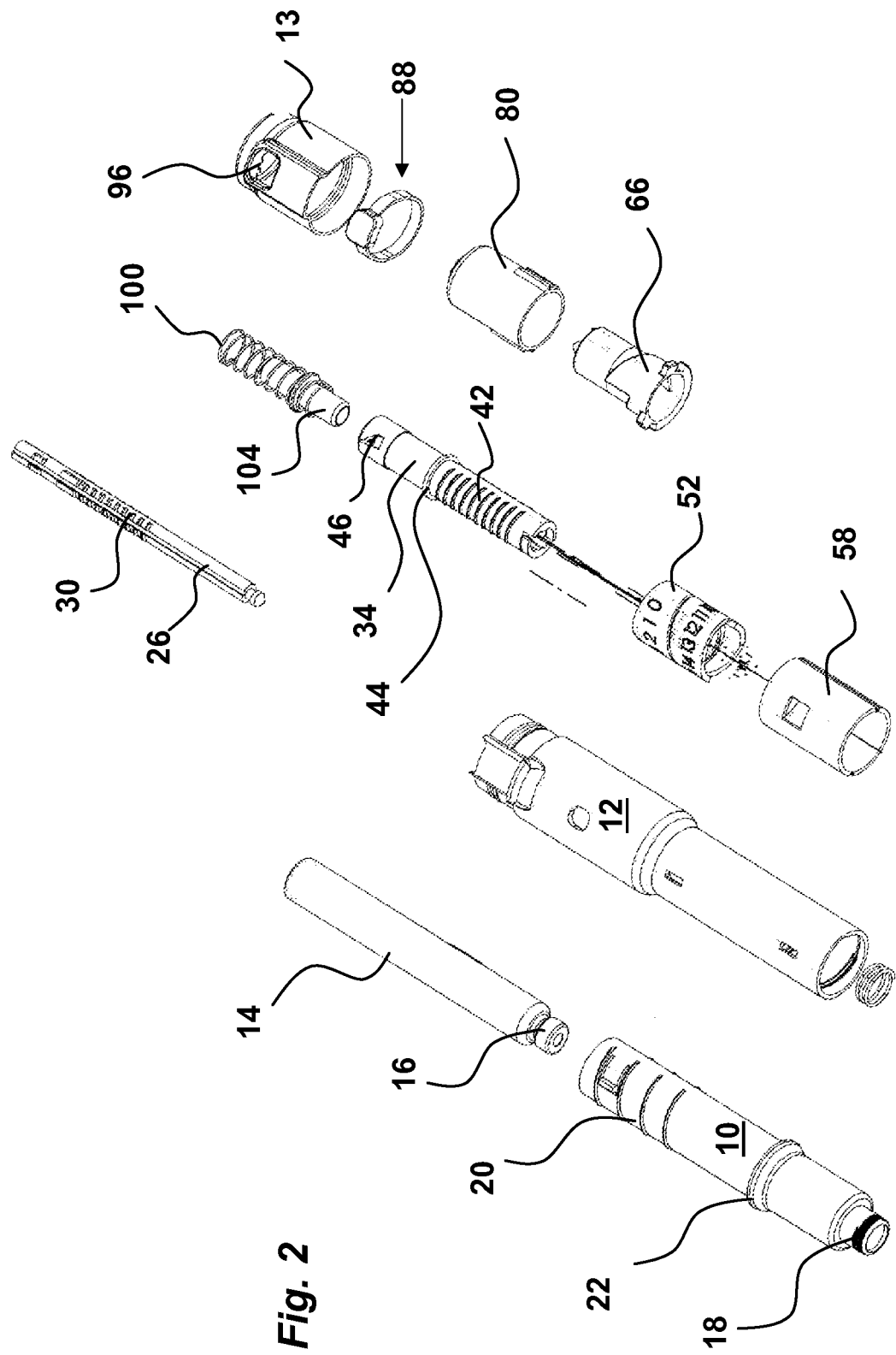
FIG. 2 shows an exploded view of the medicament delivery device of FIG. 1.
Figure 3:
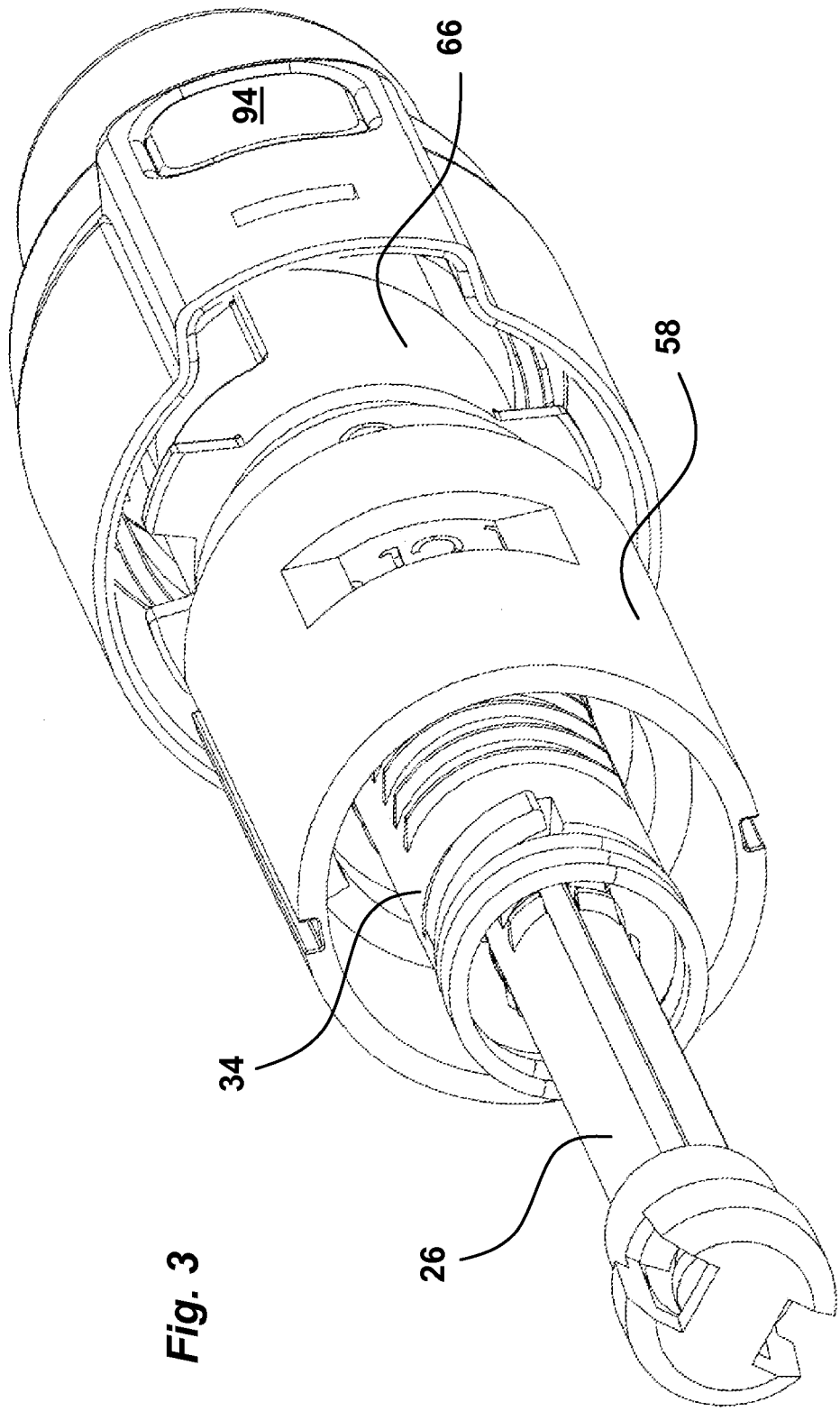
FIG. 3 shows a detailed view of a distal part of the medicament delivery device of FIG. 1.
Figure 7:
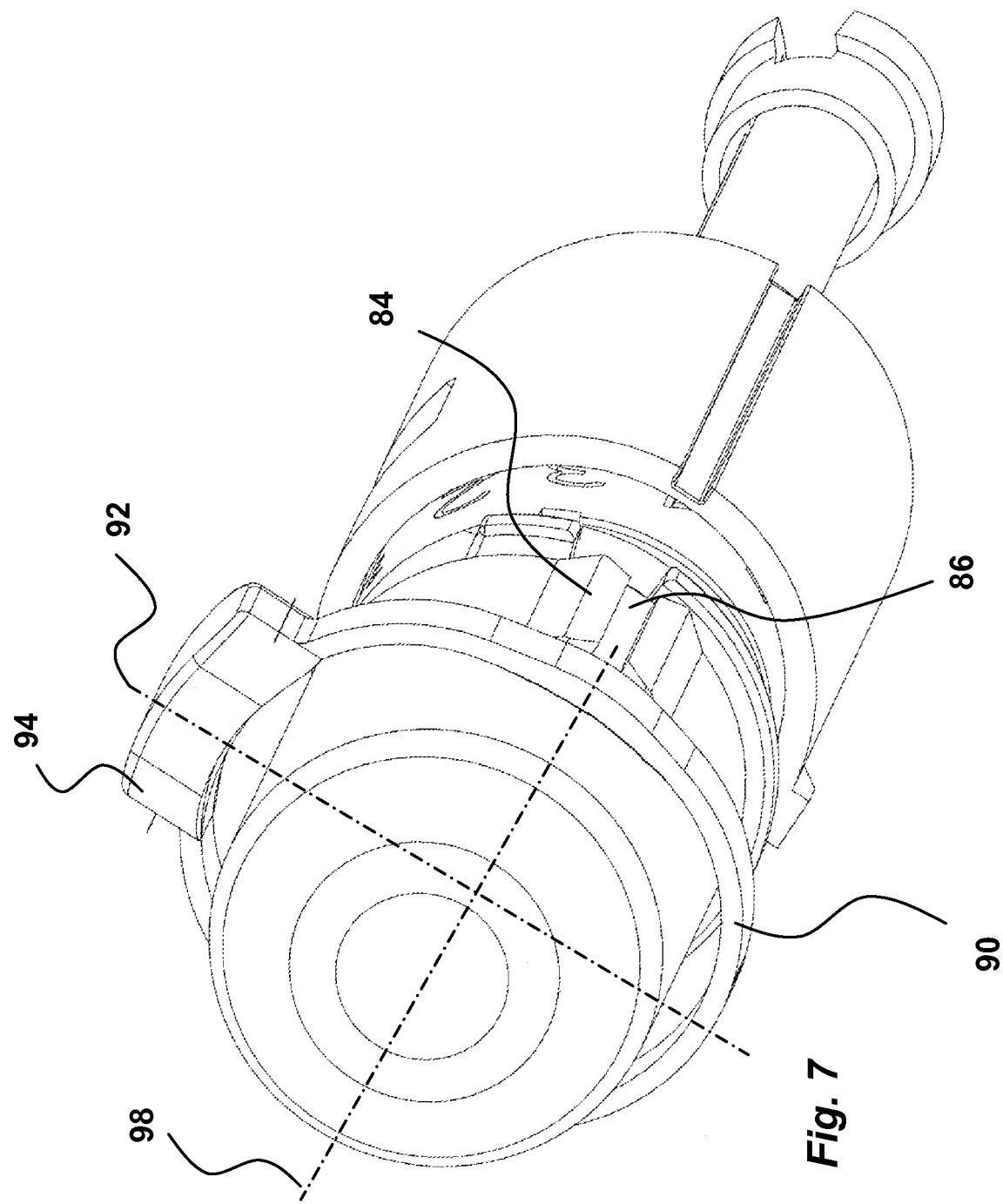
FIG. 7 shows a detailed view of FIG. 3 rotated 180°.

Further an actuation button locking member 88 is arranged, FIG. 2. As shown in FIG. 7, it comprises a ring-shaped member 90 having a somewhat oval shape when non-activated. As seen along a longer axis 92 of the oval an outwardly directed protrusion 94 is arranged, which protrusion fits into an opening 96 in the distal end cap 13, FIG. 2, such that it may be manually operated. The opposite part of the oval as seen along the longer axis 92 is in contact with a fixed housing part. As seen along a shorter axis 98 of the oval, these sections are in contact with the distal end surface of the protrusions 84 of the actuation button 80, preventing movement of the button 80.

Figure 9:
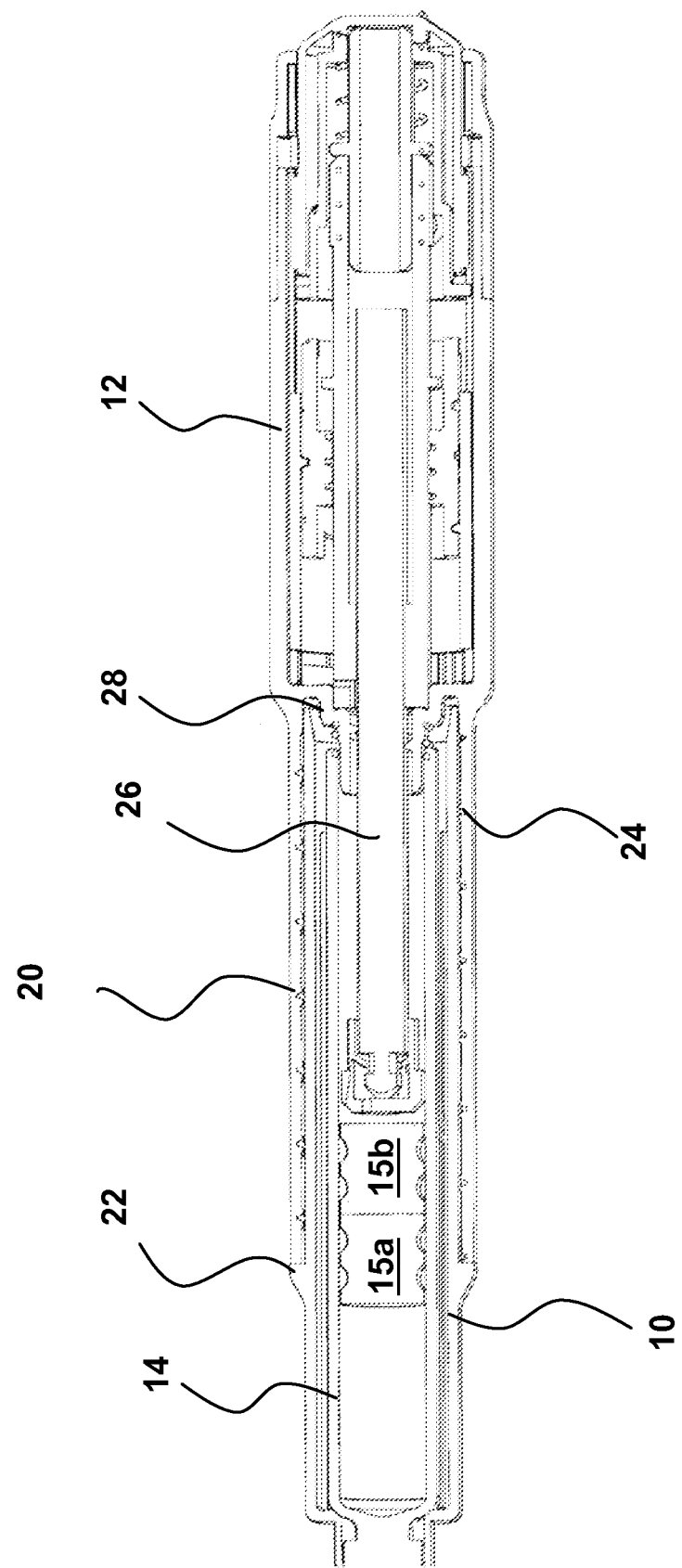
FIGS. 9, 10 are side views on cross-section of the device according to FIG. 1 in different functional positions.

The medicament delivery device is intended to function as follows. When the device is to be used for the first time, the medicament delivery device has to be prepared such that the medicament and the diluent are properly mixed. The mixing is performed in that the proximal housing part 10 is screwed into the distal part 12 by the action of the threads 20 and 24. This causes the plunger rod 26, which is locked from linear movement by the threads 30 of the plunger rod 26 in engagement with the threads 32 of the wall 28 of the distal housing part 12, and from rotation movement by the protrusions 36 of the driver 34 in engagement with the longitudinal grooves 38 of the plunger rod 26, to move forward, pushing on the stoppers 15*a*, 15*b* inside the medicament container 14 such that a passage is opened between the chambers and thus a mixing is performed. The movement between the housing parts is stopped when a proximal end surface of the distal housing part 12 is moved in contact with the circumferential ledge 22 of the proximal housing part 10, whereby the two stoppers inside the container have been moved in contact with each other, FIG. 9.

Figure 10:
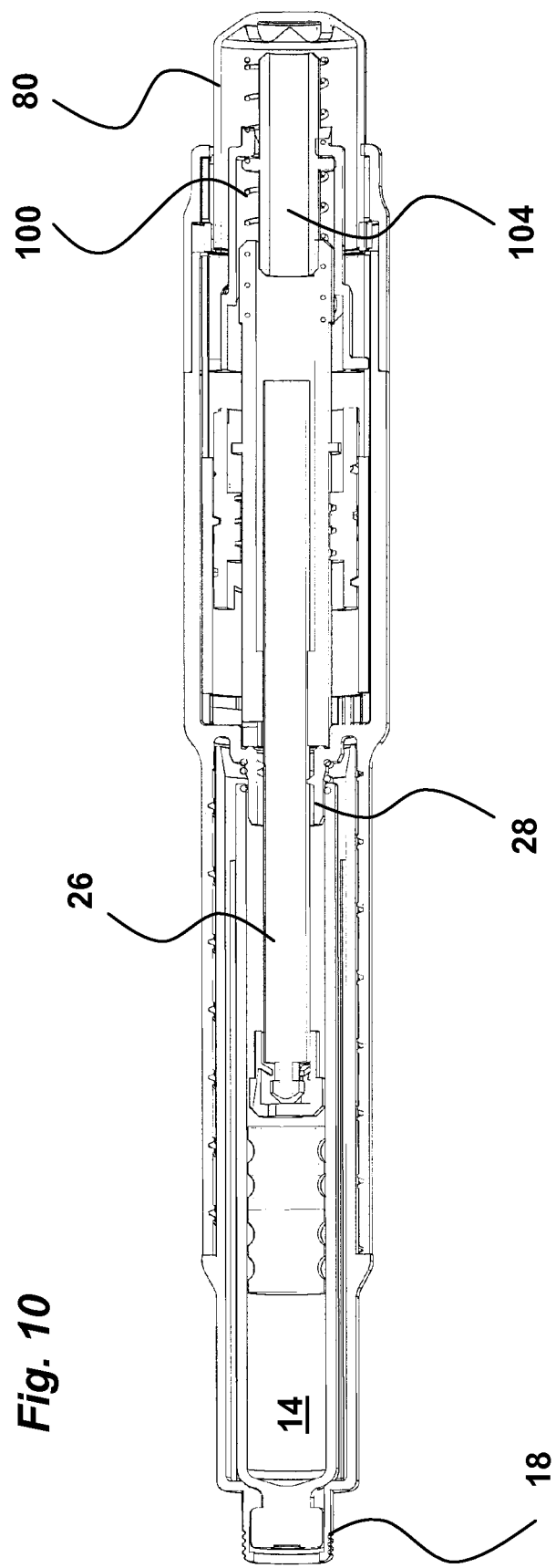
Figure 11:
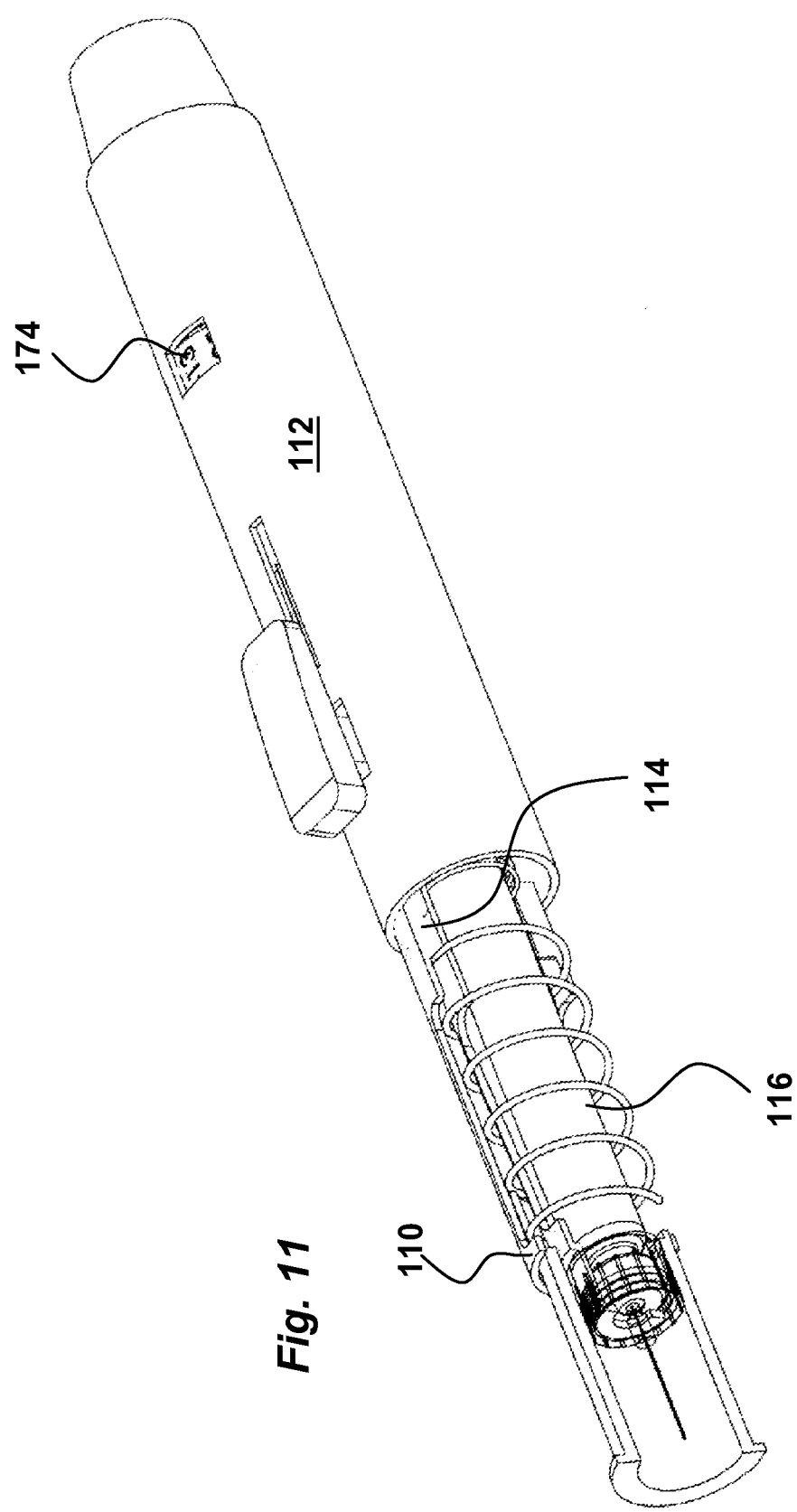
FIG. 11 shows a second embodiment of a medicament delivery device according to the present invention.
Figure 12:
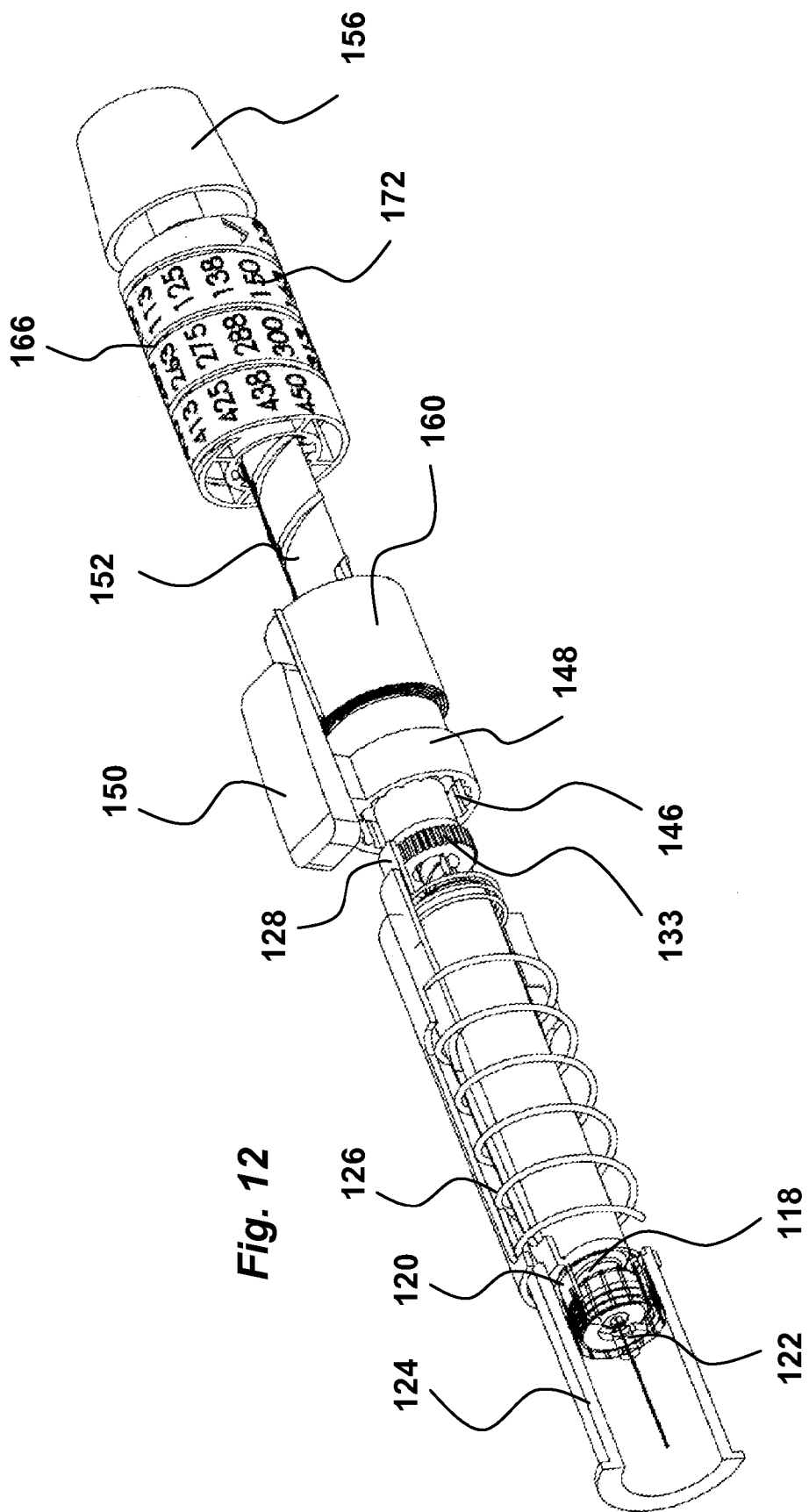
FIG. 12 shows the medicament delivery device of FIG. 11 with a distal housing part removed.
Figure 13:
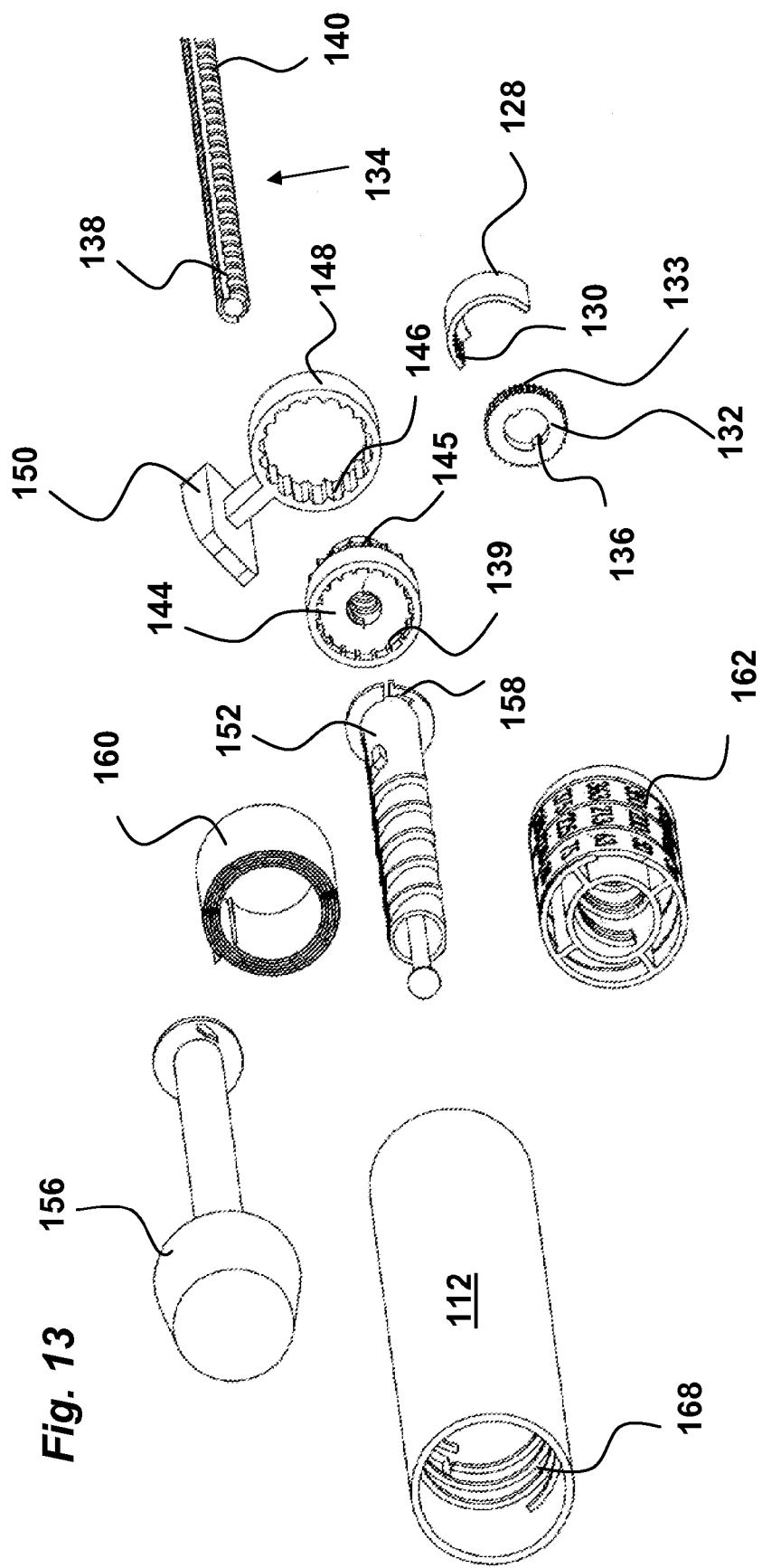
FIG. 13 shows an exploded view of the medicament delivery device of FIG. 11 rotated 180°.
Figure 14:
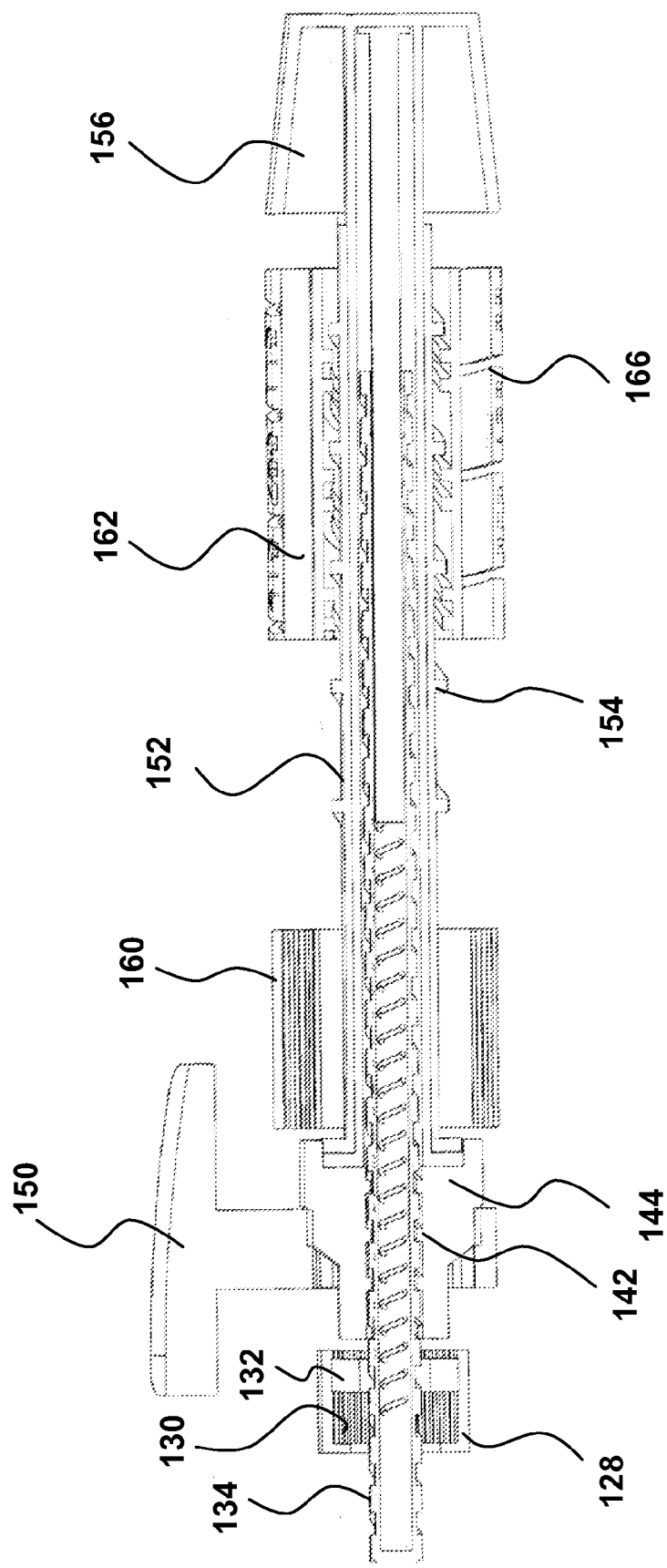
FIG. 14 shows a detailed side view in cross-section of the medicament delivery device of FIG. 11.
Figure 15:
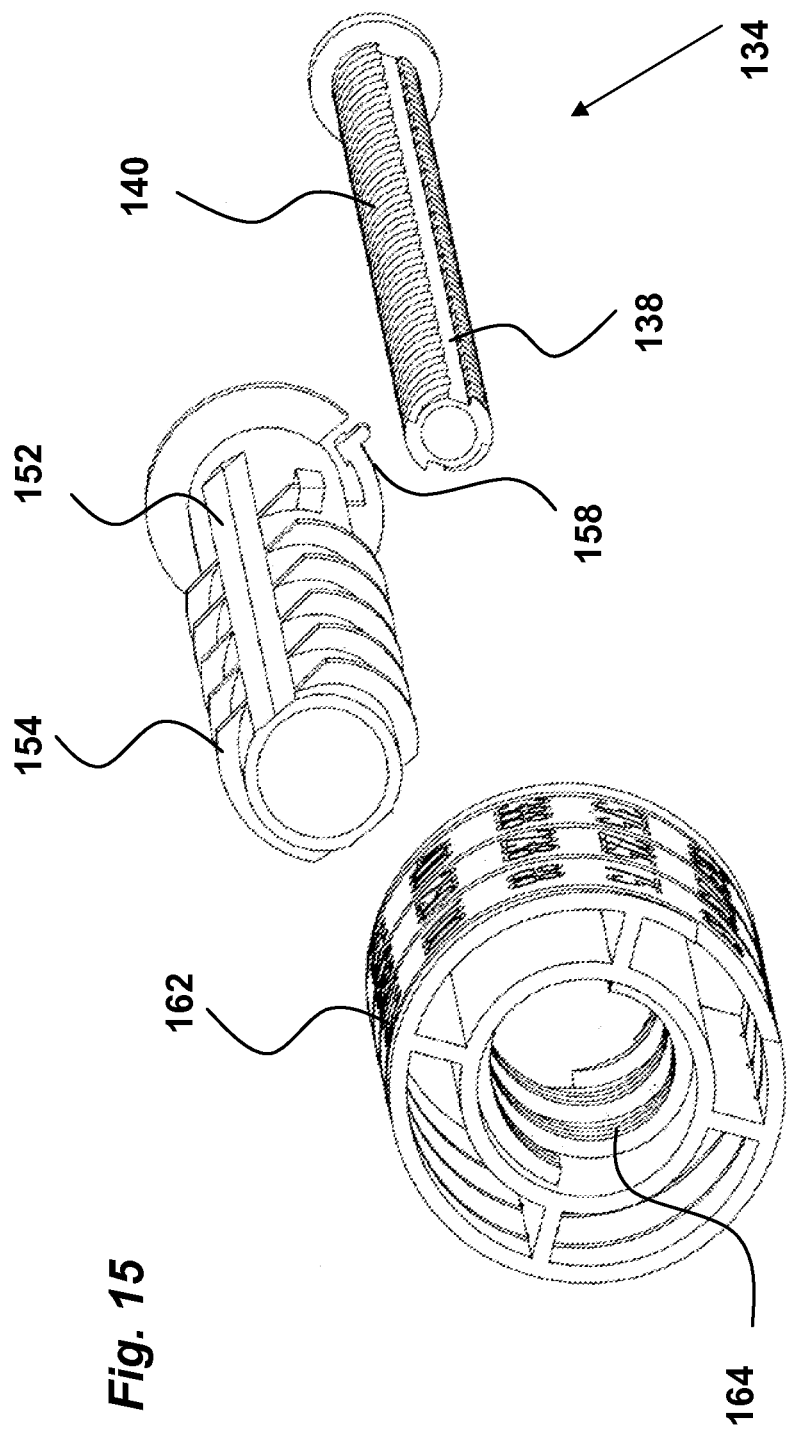
FIG. 15 shows a detailed exploded view of a dose counter mechanism of the medicament delivery device of FIG. 11 rotated 180°.

In order to deliver a dose of medicament the user attaches a medicament delivery member to the proximal neck 18 of the proximal housing part. The medicament delivery member could be an injection needle, a mouthpiece, a nozzle, and the like member capable of delivering medicament to a patient. In order to activate the device, the user presses on the protrusion 94 on the locking member 88 accessible via the opening 96 in the distal end cap 13. When the locking ring 90 is pressed the ovality is reduced, i.e. the ring becomes more circular in that the sections along the shorter axis 98 are moved outwardly radially and move out of contact with the protrusions 84. This allows the actuation button 80 together with the toggle sleeve 66 to move in the distal direction of the device due to a spring 100 acting between a ledge of a guide pin 104 and an inner end surface of the toggle sleeve 66, FIG. 10. The inclined ledge 46 of the driver 34 and the inclined 74 and stepwise 76 surfaces of the toggle sleeve 66 are positioned such that the inclined ledge 46 slides along the step-wise 76 surface. Since that surface is slightly inclined with respect to the longitudinal direction 48 of the device the toggle sleeve 66 is forced to turn somewhat. Since the actuation button 80 is rotationally locked the zig-zag surfaces 78 and 82 respectively of the actuation button 80 and the toggle sleeve 66 are displaced somewhat such that they slide along the inclined flanks of the zig-zag teeth. When finally the inclined ledge 46 has passed the stepwise surface 76, the force from the spring 100 will turn the toggle sleeve 66 in relation to the driver 34 due to the interaction of the zig-zag surfaces 78, 82 now again fitting into each other, such that the inclined ledge 46 of the driver 34 is positioned in one end of the inclined surface 74 of the toggle sleeve 66.

The medicament delivery device is now ready for delivery of a dose. The user places the medicament delivery member in the proper delivery position, e.g. the injection site in the case of an injector, and presses the actuation button 80 in the proximal direction of the device. The linear movement of the actuation button 80 causes the toggle sleeve 66 also to move linearly due to the zig-zag surfaces 78, 82 in contact with each other. The toggle sleeve 66 is prevented from turning because of one of the lips 68 of the toggle sleeve 66 being in contact with the longitudinal rib 64. Because of the contact between the inclined surface 74 of the toggle sleeve 66 and the inclined ledge 46 of the driver 34, the inclined ledge 46 will slide along the inclined surface and the driver will be turned. Because the plunger rod 26 is rotationally locked to the driver 34 due to the inwardly directed protrusions 36 of the driver in engagement with the grooves 38 of the plunger rod, also the plunger rod will be turned. Because the plunger rod 26 is in threaded engagement with the threaded passage 32 of the wall 28, the turning of the plunger rod 26 will cause it to advance, thereby advancing the stoppers 15*a*, 15*b* in the medicament container 14, which in turn causes a delivery of a dose of medicament through the medicament delivery member.

The medicament delivery stage is stopped when the inclined ledge 46 of the driver 34 comes in contact with the stepwise surface 76 of the ledge 72 of the toggle sleeve 66. When now the actuation button 80 is released it will stay in the initial depressed position because the lock ring 90 has returned to its locking position when the actuation button was depressed.

Further, the rotation of the driver 34 will activate the dose counter mechanism. The rotation of the driver will cause the dose drum 52 to rotate due to the threaded engagement between the two. However since the dose drum 52 is in threaded engagement with the thread drum 58, where the latter is rotationally locked in relation to the distal housing part 12, the dose drum 52 will be rotated, but to a much lesser extent. This is due to the different pitch between the threads of the driver/dose drum and the threads of the dose drum/thread drum. As an example the driver may be turned 180° and then the dose drum 52 will be turned 30°. This difference in pitch causes a transmission which enables or facilitates the display of indicia 56 such as dose numbers on the dose drum 52 through an opening in the distal housing part. Because of the difference in degree of turning, larger indicia may be used than otherwise, for example if the indicia would have been placed on the driver or corresponding part that is turned to such a large extent during injection.

In a second embodiment of the invention shown in the drawings 11-15, the elongated housing comprises a proximal housing part 110 detachably attached to a rear housing part 112. Inside the proximal housing part 110 a medicament container holder 114 is positioned. The medicament container holder 114 is capable of housing the medicament container 116 that in the shown embodiment is a medicament cartridge provided with a proximal neck portion 118 provided with a penetrable septum. In the distal end of the cartridge a resilient stopper (not shown) is movably arranged. It is however to be understood that other types of medicament containers may be utilized with the present invention. A proximal end of the medicament container holder is provided with a threaded neck part 120, onto which a medicament delivery member may be detachable attached, such as an injection needle 122 as shown in the drawings. It is however to be understood that other types of medicament delivery members may be utilised, such as mouth-pieces, nozzles, and the like. It is also to be understood that other types of attachment means may be utilised, such as bayonet fittings, snap-on fasteners and the like. A generally tubular needle cover 124 is arranged slidable inside said proximal housing part 110, which needle cover 124 is urged in the proximal extended direction by a needle cover spring 126.

The actuation mechanism of the second embodiment comprises:
- a lock sleeve 128 and a lock nut 132 releasibly connected to each other, wherein the lock nut is slidably connected to the plunger rod;
- a drive nut 144 and a locking ring 148 having an actuation button 150, wherein the drive nut is releasibly connected to the locking ring and to the driver, and wherein the drive nut is threadedly connected to the plunger rod; and
- a drive force member 160 having a first end connected to the housing and a second end connected to the driver, such that said drive force member is capable of rotating said driver upon actuation. The function of which will be described below.

The lock sleeve 128 is arranged at the proximal end of the distal housing part 112, arranged slidable in the longitudinal direction but locked rotationally and urged in the proximal direction by a spring (not shown). The lock sleeve 128 is arranged with splines-like protrusions 130 on an inner circumferential surface, which splines are arranged to cooperate with the lock nut 132 having splines-like protrusions 133 on an outer circumferential surface and being arranged around a plunger rod 134, which in turn is arranged in the distal housing part 112 with its proximal end in contact with the stopper of the medicament container 116. The lock nut 132 is provided with radially inwardly directed ledges 136, which ledges fit into longitudinal grooves 138 on the plunger rod 134. The plunger rod 134 is further arranged with threads 140 on its outer circumferential surface. The threads 140 are arranged to cooperate with corresponding threads 142 arranged in a central passage of the drive nut 144. The outer circumferential surface of the drive nut 144 is arranged with splines-like protrusions 145 extending in the longitudinal direction, which splines 145 are arranged to cooperate with corresponding splines-like protrusions 146 arranged on an inner circumferential surface of the locking ring 148. The outer surface of the locking ring is arranged with a post, which protrudes through an opening in the distal housing part. The locking ring is arranged slidable in the longitudinal direction of the device by the actuation button 150 attached on the post.

The driver 152, hereafter named dose setting driver, has a generally tubular elongated shape 152 and is coaxially arranged on the plunger rod 134. The outer circumferential surface of the dose setting driver 152 is arranged with threads 154 of a certain pitch.

The device further comprises a dose setting knob 156 which is attached to the dose setting driver 152 such that the dose setting driver 152 may be rotated. At the proximal end of the dose setting driver a ratchet 158 is arranged and intended to cooperate with teeth 139 arranged in an inner circumferential surface at the distal end of the drive nut 144 such that the dose setting driver 152 may only be rotated in one direction in relation to the drive nut 144. Further, the drive force member 160, in the shown embodiment a spiral spring, is arranged around said dose setting driver 152 and attached to it with one end. The other end of the spiral spring is attached to the distal housing part 112, or any other part fixed in relation to the distal housing part. The dose drum 162 is coaxially arranged on the dose setting driver, and is arranged with threads 164 on its inner circumferential surface, which threads 164 are arranged to cooperate with the threads 154 of the dose setting driver 152. Further threads 166 of a certain pitch are arranged on the outer surface of the dose drum 162, which outer threads 166 are arranged to cooperate with threads 168 on an inner surface of the distal housing part 112 or on an inner surface of another part fixed in relation to the distal housing part 112.

The device of the second embodiment is intended to function as follows. The device is commonly delivered with the proximal and distal housing parts 110, 112 separate. The user places a medicament container 116 in the medicament holder 114 of the proximal housing part 110 and then attaches the proximal housing part to the distal housing part. When not connected, the plunger rod 134 is urged in the proximal direction by a spring 170 arranged inside the plunger rod 134 with a proximal end acting on a proximal end wall of the plunger rod and with a distal end acting on a surface fixed in relation to the distal housing part 112. When the user pushes the proximal housing part towards the distal housing part, the plunger rod 134 is urged inside the distal housing part 112 against the force of the spring 170 in that the plunger rod 134 is free to rotate because the lock 132 nut is not held in position by the lock sleeve 128, and due to the threaded connection with the drive nut 144, until the distal end surface of the medicament container 116 comes in contact with the lock sleeve 128, which in turn is pushed in the distal direction, whereby the splines 130 of the lock sleeve 128 comes in contact with the splines 145 of the lock nut 132, whereby the lock nut 132 becomes locked rotationally, which in turn locks the plunger rod 134. The two housing parts are now attached to each other with the plunger rod 134 in proper contact with the stopper of the medicament container 116.

The user then pushes the needle cover 124 into the proximal housing part 110 against the force of the needle cover spring 126 and attaches a proper medicament delivery member 122 to the neck portion 120 of the proximal housing part 110. The next step is to set a prescribed dose. The user then turns the dose setting knob 156 at the distal end of the device. This causes the dose setting driver 152 to rotate in relation to the drive nut 144, which rotation causes the spiral spring 160 to tension.

The dose setting driver 152 is prevented from rotating back by the ratchet 158. The rotation further causes the dose drum 162 to rotate due to the threaded engagement between the dose setting driver 152 and the dose drum 162. However, there is a threaded connection between the dose drum 162 and the distal housing part 112 and the pitch of the latter threaded connection is chosen lesser than the pitch of the threaded connection of the dose sleeve/dose drum, whereby the dose drum 162 is rotated a smaller rotational angle than the dose sleeve 152. The outer surface of the dose drum 162 is provided with indicia 172 such as dose size, which are visible through an opening or window 174 in the distal housing part. Thus when the prescribed dose is visible in the window 174, the user can stop the turning of the dose setting knob 156. Due to the difference in pitch a transmission is obtained whereby the dose drum 162 is rotated to a much lesser extent than the dose setting driver 152, which enables the indication of dose sizes on the dose drum, which would not be possible if the dose drum 162 was rotated to the same extent as the dose setting driver.

When a dose is to be delivered the proximal end of the device is positioned at the dose delivery site, which could be an injection site or adjacent the mouth of the patient. The actuation button 150 is then slid in relation to the housing whereby the splines 146 of the lock ring 148 are moved out of contact with the splines 145 of the drive nut 144. Because of the connection between the drive nut 144 and the dose setting driver 152, where the latter is attached to the tensioned spiral spring 160, the dose setting driver 152 and the drive nut 144 are free to rotate due to the force of the spring 160. The rotation of the drive nut 144 causes the plunger rod 134 to be moved forward due to the threaded connection between the drive nut 144 and the plunger rod 134 and the rotational lock between the plunger rod 134 and the lock nut 132. This forward movement of the plunger rod 134 causes it to act on and move the stopper of the medicament container 116 forward whereby a dose of medicament is expelled through the medicament delivery member 122. The rotation of the dose setting driver 152 causes the dose drum 162 to rotate back due to the threaded connection, but as described above the dose drum 162 is rotated back to a lesser extent than the rotation of the dose setting driver 152. The injection is completed when the dose drum has reached its initial rest position, which is displayed in the window 174.

When the device is removed from the delivery site the needle cover 124 is pushed into its proximal extended position by the needle cover spring 126. The user can now remove the dose delivery member and discard it, after which the device may be stored until the subsequent delivery occasion.

It is to be understood that the embodiments described above and shown in the drawings only are to be regarded as non-limiting examples of the invention and that it may be modified in many ways within the scope of the patent claims. In this context, even if the present invention has been described in connection with a manual medicament delivery device, it may as well be used with a device having an automatic delivery function.

The invention claimed is:

1. A medicament delivery device, comprising:
   an elongated housing having a window and arranged to contain a medicament container that contains a number of doses;
   a dose counter mechanism, comprising a dose drum arranged with dose indicia on an outer surface of the dose drum visible through the window;
   a rotatable driver connected to the dose drum;
   a plunger rod arranged to act on the medicament container for expelling a dose of medicament; and
   an actuation mechanism connected to the rotatable driver and to the plunger rod when the medicament delivery device is actuated, the actuation mechanism comprising a toggle sleeve and an actuation button, wherein the actuation button is operably connected to the toggle sleeve that is operably connected to the rotatable driver such that the rotatable driver is rotated when the actuation button is actuated;
   wherein the dose drum includes internal threads for engaging corresponding threads on the rotatable driver, the internal threads having a first pitch; and the dose drum includes external threads for engaging corresponding threads arranged in fixed relation to the housing, the external threads having a second pitch that is less than the first pitch of the threads on the rotatable driver, such that when the rotatable driver is rotated a certain angular distance, the dose drum is rotated a lesser angular distance.

2. The medicament delivery device of claim 1, wherein the actuation button and the toggle sleeve are slidable in a proximal direction of the device, and the toggle sleeve comprises surfaces inclined with respect to a longitudinal direction of the device and arranged to cooperate with ledges on the rotatable driver, such that when the actuation button is moved in the proximal direction, the inclined surfaces act on the ledges for turning the rotatable driver.

3. The medicament delivery device of claim 2, further comprising a locking member configured for locking the actuation button in a non-actuated state until the locking member is manually activated, whereby the actuation button is moved in a distal direction of the device for subsequent actuation by pressing manually in the proximal direction.

4. The medicament delivery device of claim 1, wherein the dose indicia are configured for displaying a number of doses delivered.

5. The medicament delivery device of claim 4, wherein the actuation button and the toggle sleeve are slidable in a proximal direction of the device, and the toggle sleeve comprises surfaces inclined with respect to a longitudinal direction of the device and arranged to cooperate with ledges on the rotatable driver, such that when the actuation button is moved in the proximal direction, the inclined surfaces act on the ledges for turning the rotatable driver.

6. The medicament delivery device of claim 5, further comprising a locking member configured for locking the actuation button in a non-actuated state until the locking member is manually activated, whereby the actuation button is moved in a distal direction of the device for subsequent actuation by pressing manually in the proximal direction.

7. The medicament delivery device of claim 1, further comprising a dose setting knob operably connected to the rotatable driver, whereby rotation of the dose setting knob rotates the rotatable driver and to a lesser extent rotates the dose drum until a desired dose quantity is displayed.

8. The medicament delivery device of claim 7, wherein the actuation mechanism comprises:
   a lock sleeve and a lock nut releasably connected to each other, wherein the lock nut is slidably connected to the plunger rod;
   a drive nut and a locking ring having the actuation button, wherein the drive nut is releasably connected to the locking ring and to the rotatable driver, and the drive nut is threadedly connected to the plunger rod; and
   a drive force member having a first end connected to the housing and a second end connected to the rotatable driver, such that the drive force member is configured for rotating the rotatable driver upon actuation.

9. The medicament delivery device of claim 8, wherein the drive force member comprises a spiral spring that is tensioned when the dose knob and the rotatable driver are turned for setting a dose.

* * * * *